United States Patent [19]
Barber et al.

[11] Patent Number: 6,017,541
[45] Date of Patent: Jan. 25, 2000

[54] IMMUNOGENS FOR THE PRODUCTION OF COCAINE-HYDROLYZING CATALYTIC ANTIBODIES

[76] Inventors: Brian H. Barber, 1428 Broadmoor Avenue, Mississauga, Ontario, Canada, L5G 3T5; Neal den Hollander, 606 Tedwyn Drive, Mississauga, Ontario, Canada, L5A 1K2; Jiri J. Krepinsky, 810 Srigley Street, Newmarket, Ontario, Canada, L3Y 1X7; M. Younus Meah, 1117 McIntyre Dr., Ann Arbor, Mich. 44105

[21] Appl. No.: 08/906,151

[22] Filed: Aug. 5, 1997

Related U.S. Application Data

[63] Continuation of application No. 08/259,004, Jun. 13, 1994, Pat. No. 5,730,985.

[51] Int. Cl.$^7$ .......................... A61K 39/385; C07K 16/00
[52] U.S. Cl. ..................... 424/193.1; 424/194.1; 424/184.1; 435/188.5; 560/103; 560/109; 546/129; 546/198; 558/198
[58] Field of Search ............................. 424/189.1, 193.1, 424/194.1, 184.1, 188.5; 435/188.5; 546/129, 198; 560/103, 109; 558/198

[56] References Cited

U.S. PATENT DOCUMENTS

| | | | |
|---|---|---|---|
| 4,078,049 | 3/1978 | Felix et al. | 436/542 |
| 5,202,270 | 4/1993 | Ungemach et al. | 436/537 |
| 5,274,080 | 12/1993 | MacCoss et al. | 530/389.9 |
| 5,436,028 | 10/1995 | Landry et al. | 427/96 |
| 5,730,985 | 3/1998 | Barber et al. | 424/193.1 |

FOREIGN PATENT DOCUMENTS

WO-A-93-20076  10/1993  WIPO.

OTHER PUBLICATIONS

Science (Washington, D.C., 1883–); Scieas, 00368075; 93; vol. 259 (5103); pp. 1899–1901, Columbia Univ.; Coll. Physicians Surg.; New York, 10032, NY, USA; (US) Landry D. W. et al 'Antibody–catalyzed degradation of cocaine' Bioorg. Med. Chem. Lett. (BMCLE8, 0960894X; 93; vol. 3 (2); pp. 309–312, Searle Res. Dev.; Dep. Med Chem.; Skokie 60077, II., USA (US) Chandrakumar N.S. et al 'Phenylphosphonate monoester analogs of cocaine. Potential haptens for the generation of catalytic antibodies'.

Aldrich Catalog Handbook of Fine Chemicals p. 57, 1990.

Landry et al. Science vol. 259: 1899–1901, 1993.

F.I. Carroll and A.H. Lewin, in Emerging Technologies and New Directions in Drug Abuse Research (R.S. Rapaka, A. Makriyannis, and M.J. Kuhar, Eds.), NIDA Research Monograph #112, Superintendent of Documents, U.S. Government Printing Office, Washington DC 1991, 284–299.

K.D. Janda, S.J. Benkovic, and R.A. Lerner, Science 224, 437–440 (1990).

S.J. Pollack, P. Hsiun, and P.G. Schultz, J. Am. Chem. Soc. 111, 5061–5963 (1989).

N.S. Chandrakumar, C.C. Carron, D.B. Meyer, P.M. Beardsley, S.A. Nash, L.L. Tam, and M. rafferty, Bioorg. Med. Chem. Lett. 3, 309–312 (1993).

D.w. Landry, K. Zhao, G.X.–Q. Yang, M. Glickman, T.M. Georgiadis, Science 259, 1899–1901 (1993).

*Primary Examiner*—Frank C. Eisenschenk
*Assistant Examiner*—Ali R. Salimi
*Attorney, Agent, or Firm*—Shoemaker and Mattare Ltd.

[57] ABSTRACT

Methods are described for the rapid synthesis in satisfactory yield of methyl ecgonine phenylphosphonates as analogues of transition states for the hydrolysis of the benzoyl ester of an ecgonine derivative, namely cocaine, and their linking to carrier proteins, for the purpose of using them as immunogens. The resulting immunogens elicit the formation in experimental animals of antibodies able to promote the hydrolysis of cocaine. Both these catalytic anti-cocaine antibodies and the immunogens themselves are potentially useful for the treatment of individuals seeking to avoid the pharmacological effects of cocaine and in diagnostic applications.

5 Claims, 9 Drawing Sheets

FIG. 1.

FIG. 2A. Scheme 1

Scheme 2

IMMUNOGENS FOR THE PRODUCTION OF COCAINE-HYDROLYZING CATALYTIC ANTIBODIES

This is a continuation of application Ser. No. 08/259,004 filed Jun. 13, 1994 (now U.S. Pat. No. 5,730,985).

FIELD OF THE INVENTION

This invention relates to the preparation, by chemical synthesis, of methyl ecgonine phosphonates as analogues of transition states for the hydrolysis of the benzoyl ester bond in cocaine, and their linking to carrier proteins. By these methods, the phosphonates are produced rapidly in satisfactory yields. The resulting immunogens elicit the formation, in experimental animals, of antibodies capable of hydrolysis of cocaine. Both these catalytic antibodies and the immunogens used to induce them are potentially useful for the treatment of individuals at risk for the abuse of cocaine. Such compounds also are useful for immunodiagnostic purposes with respect to such individuals.

BACKGROUND TO THE INVENTION

Cocaine is an ecgonine ester compound of the formula:

(ref. 1—a list of references appears at the end of the descriptive text. This paper provides an overview of nomenclature. Compound names used in this specification are defined in this article).

The abuse of cocaine represents a major threat to the social and economic fabric of many developed countries. Although several dopaminergic agents and the tricyclic antidepressant desipramine have been clinically tested, effective therapies to assist drug-addicted individuals in their return to drug-free life still are not available. Mobilizing the immune system to "block" drugs from reaching their sites of action in the central nervous system represents a potential, but as yet poorly explored, means of therapeutic intervention.

It is well known that drugs of abuse can be rendered inactive by disrupting a structural feature either required for the interaction with their respective receptors or necessary for transport. Thus, in cocaine, the presence of the benzoyl ester moiety in the molecule is essential for maintaining its activity. Therefore, if antibodies possessing cocaine-specific esterase activity could be induced, such catalytic antibodies could potentially act in vivo to neutralize the pharmacological effects of the drug in an immunized individual. Enzymes and abzymes (otherwise known as catalytic antibodies) apparently employ a similar mechanism for the catalysis of hydrolysis.

Abzymes, as any catalyst, lower the energy required to proceed through the transition state between the starting compound and the respective reaction products. Thus, a catalytic antibody binds to and stabilizes a shape corresponding to the transition state with little or no energy expenditure on the part of the substrate.

Depending on the presence of other factors, the substrate then could proceed to the product or to return to its starting form. In the case of hydrolysis, water must be present, since the hydroxyl group of the water, due to its nucleophilic properties, enters the protransition state and forms the proper transition state for the hydrolysis, and the hydrolysis then takes place. Therefore, a catalytic antibody should be ideally made against such a transition state. However, since transition states are unstable by definition, antibodies have to be made against stable molecules which structurally mimic the transition state (transition state analogs). It has been established that the transition state (ref. 2) for carboxylate ester hydrolysis is centered around unstable formally "pentavalent" carbon, and consequently it can be mimicked by a stable phosphonate ester (ref. 3) since phosphorus is stable pentavalent and shapes and charge distribution of both resemble each other fairly closely. However, esters are among the most common functional groups in living organisms, and thus it is essential that the abzyme is devoid of any general esterase activity and is endowed with very specific benzoyl esterase activity in the context of the cocaine molecule. To achieve this objective, it is crucial that the transition state analog does not disrupt structural features defining specificity of interaction between cocaine and the recognition moiety of the abzyme. If this condition is not met, the antibodies made against such transition state analogs will not be sufficiently specific to be practical.

It is recognized that polar groups in a molecule tend to be the focal point of B-cell (i.e. antibody reactive) epitopes. In cocaine, there are three polar groups, namely the bridgehead nitrogen (methylated), the methyl ester, and the benzoyl ester. As explained above, since the benzoyl ester is the target for the hydrolysis by a catalytic antibody, the transition state for the hydrolysis of the benzoyl ester can be mimicked by substituting phenylphosphonate for benzoate in the cocaine molecule. Such a phosphonate has to be linked to a carrier protein, as is conventionally required to enhance the immunogenicity of small molecules. Linkers have to be of appropriate length to maintain the transition state analog at the optimal distance from the antibody binding site. If the linker is too short, the carrier protein could interfere sterically, while, if it is too long, the linker may fold back to the protein, so that the transition state analog would adhere to the protein molecule or its fragments after processing.

Four sites for anchoring the linker on the cocaine molecule are identifiable (listed in order of increasing synthetic difficulty):

(i) a substitution of the N-methyl group by an alkyl chain, the other end of which is bound to a carrier protein (e.g. utilizing the amino group of a lysine in the carrier protein);

(ii) a substitution of the methyl ester by a bifunctional molecule, such as a dicarboxylic acid, the other end of which again is bound to a carrier protein, either directly or through an extension chain;

(iii) p-substitution at the phenyl ring of the phenylphosphonate group with a chain linked again to a carrier protein directly or through an extension chain; and (iv) a substitution of a ring hydrogen in the ecgonine ring system by a chain of carbon atoms, the other end of which is functionalized so that a bond to a carrier protein can be formed.

Although the third choice (iii) appears to be the best one since it disturbs least of all the important recognition elements of cocaine and remains still within the reach of organic synthetic methodology for a possible future mass production, an attempt was described to link a phenylphosphonate analog of cocaine (ref. 4) via an alkyl chain originating in the nitrogen function utilizing anchoring site (i).

Although a number of binding monoclonal antibodies have been isolated, none of them was endowed with the desired catalytic activity, thus confirming the conclusion of the discussion hereinabove.

Figure 1:
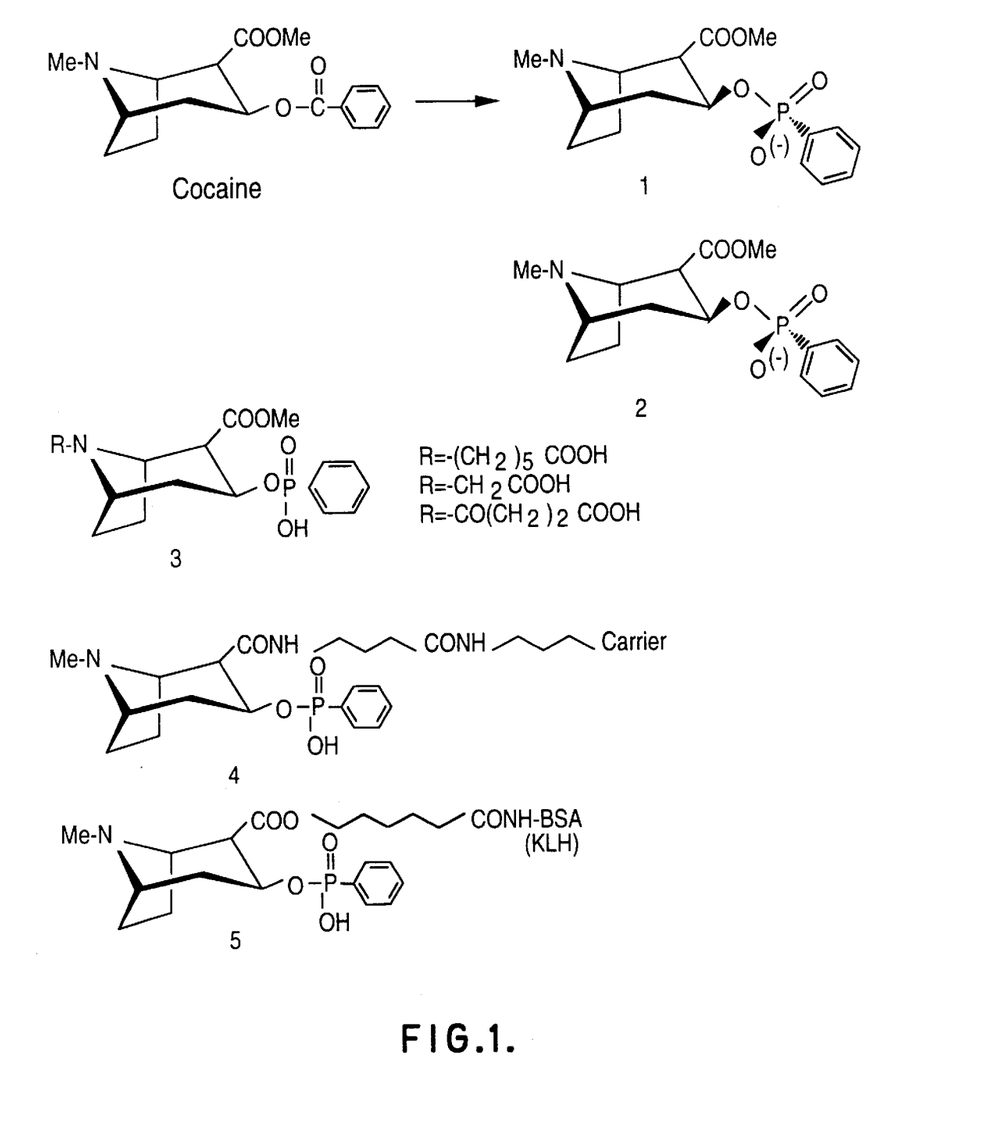
FIG. 1 contains a schematic illustration of cocaine and certain derivatives thereof, referred to herein as compounds 1 to 5.

At least two attempts have been made utilizing the anchoring site (ii). The transition state analog using a specific linker (ref. 5) was described that using the state of the art methodology made possible isolation of two catalytic monoclonal antibodies with small, albeit detectable catalytic activity. Identical transition state analogs using a different linker to BSA or KLH (compounds 5a, 5b, FIG. 1—ref. 6) gave a polyclonal binding antibody in rabbits, and several binding monoclonal antibodies, none of them endowed with catalytic activity. This result could be expected, as it has been outlined hereinabove.

SUMMARY OF INVENTION

The present invention provides certain novel compounds which are methyl ecgonine phosphonate ester derivatives. Accordingly, in one aspect of the present invention, there is provided a novel methyl ecgonine phosphonate ester having the formula:

wherein R is selected from:
  (a) a functional group,
  (b) the group (-Y-functional group), wherein Y is a linker group, including an alkylene radical, and
  (c) the group (-Y-carrier molecule), wherein Y is a linker group, including an alkylene radical.

The compounds where R is a functional group are useful intermediates in the preparation of the compounds where R is the group (-Y-functional group), which, in turn are useful intermediates in the preparation of the compounds where R is the group (-Y-carrier molecule). The compounds where R is a functional group also are useful as intermediates in the preparation of the compounds where R is the group (-Y-carrier molecule). The preparation of such intermediate compounds is described below.

The compounds where R is the group (-Y-carrier molecule) are immunogens capable of inducing antibodies which accelerate the hydrolysis of cocaine in an addicted animal, particularly a human.

As noted above, the linkage between the phosphonate ester and the carrier protein should be of sufficient length that the carrier protein does not interfere with the esterase activity of the overall molecule. If the linkage is too short, then the carrier protein may interfere sterically with the phenylphosphonate while, if the linkage is too long, then the carrier protein may fold back and again interfere sterically. The linkage may comprise covalently-bonded functional groups and carbon atoms in an alkylene radical. In general, the linkage may comprise from about 5 to about 15 linearly-linked atoms, preferably about 8 to about 10 atoms.

Accordingly, in another aspect of the invention, there is provided an immunogenic composition useful for the immunization of an animal, comprising an effective amount of the novel methyl ecgonine phosphonate ester provided herein in which R is (-Y-carrier molecule) or an antibody raised thereto, and a pharmaceutically-acceptable carrier. The invention, in a further aspect, provides a method for the treatment of a cocaine-addicted animal, particularly a human, which comprises administering to the animal an immunogenic composition as just described to generate cocaine-neutralizing antibodies in the animal.

The latter compounds, i.e. the compounds where R is the group (-Y-carrier molecule), also are useful in diagnostic applications. In one such diagnostic application, the compounds can be used to screen persons for cocaine use by testing serum taken from a person for the generation of antibodies to the compounds using any convenient assaying technique, such as an ELISA assay.

The latter compounds also are useful in generating antibodies to the compounds in an animal, which antibodies themselves, which may be monoclonal or polyclonal, are useful in diagnostic assays and also in therapy, as a result of their cocaine-neutralizing property. Such antibodies also are useful for research purposes with respect to cocaine addiction.

One therapeutic application, which may have particular application to neonates of cocaine-addicted mothers, involves removing serum from an addicted animal, treating the serum with the cocaine-hydrolyzing antibodies, preferably with the antibodies in an immunobilized form, and returning the treated serum to the animal.

The novel methyl ecgonine phosphonate esters of the invention may be prepared by any convenient synthesis procedure. However, it is preferred to effect substitution of methyl ecgonine (i.e. 2β-methoxycarbonyltropan-3β-ol) at the free hydroxyl group by an activated phosphonyl substituted phenyl compound which is also substituted by a protected functional group. This procedure is a novel chemical process and constitutes a further aspect of this invention.

GENERAL DESCRIPTION OF THE INVENTION

As described above, in one aspect, we have now discovered how to prepare an immunogen capable of inducing antibodies which accelerate the hydrolysis of cocaine utilizing methyl ecgonine phenylphosphonate p-substituted with a tether or a linker to a carrier protein (=cocaine-based immunogen, or CBI). The cocaine-based immunogen can be prepared from ecgonine methyl ester and phenylphosphinic dichloride substituted in the p-position with a carbon-based chain functionalized at its other end. This functionality may comprise, but is not limited to, a carboxylic group. The product of this reaction then can be linked to a carrier molecule comprising, but not limited to, a serum albumin, either directly or by using a carrier molecule containing a tether ending with a functional group capable of forming a linkage with a transition state analog derivative described above. An example of such a group is an amino group. Although we have described the combination of a carboxylic and an amino group to form a linkage, a combination of other two groups, well known in the art, can be utilized.

The cocaine-based immunogen prepared by methods just described may be utilized in the immunization of mice to produce hybridomas capable of making monoclonal anti-cocaine antibodies having esterase activity by methods well established in the field of immunology. Such catalytic mouse anti-cocaine monoclonal antibodies may form the basis for constructing "humanized" monoclonal antibodies of therapeutic value by the application of established genetic engineering technologies. Alteratively, the cocaine-based immunogen may be utilized for immunization of animals suitable for making anti-cocaine polyclonal sera (from which antibodies may be separated by purification, if desired), similarly having esterase activity. The ultimate utilization for the cocaine-based immunogen is foreseen to be immunization of humans with such cocaine-based immunogens containing a carrier suitable for human use. Such immunization would maintain the presence of the anti-cocaine esterase activity in the body so that the use of cocaine by an immunized person would not produce the desired physiological effects but rather the cocaine would be hydrolyzed in the human body.

The present invention provides, in a further aspect thereof, a process for the preparation of cocaine-based immunogens, which comprises the steps of:

a) forming a reaction product of a methyl ecgonine phenylphosphonate p-substituted with a tether or linking group to a carrier protein or other carrier molecule, such as a peptide or polypeptiae, or a reaction product having a tether or linking group terminating with a functional group, which permits the formation of a linkage to a carrier protein or other carrier molecule;

b) activating the carrier molecule, if necessary, by, but not limited to, derivatization of the carrier molecule with a suitable group capable of binding to the functional group at the end of the tether or linking group by a covalent bond stable under physiological conditions; and c) subjecting the reaction product having a tether or linking group terminating with a functional group to a condensation reaction with the activated carrier to form a desired carrier-linked product.

The cocaine-based immunogen produced by these procedures may be usually isolated as a solid. The cocaine-based immunogen then may be used:

(i) for immunization of animals to prepare monoclonal antibodies utilising any convenient protocol;

(ii) for immunization of animals to prepare polyclonal antibodies utilising any convenient protocol;

(iii) for the treatment of humans for cocaine addiction by way of immunization; and (iv) for the diagnosis of addiction or exposure of a person to cocaine.

The monoclonal antibodies or polyclonal sera and antibodies derived therefrom may be used as is or in humanized form for the treatment of humans for cocaine addiction by in vivo administration or in vitro serum treatment.

DESCRIPTION OF PREFERRED EMBODIMENTS

In order that the invention may be better understood, preferred embodiments now are described by way of example only, with reference to the accompanying reaction schemes and diagrams. In one preferred form of the invention, methyl ecgonine (compound 9) or 2β-methoxycarbonyltropan-3β-ol may be transformed into the cocaine-based immunogen (compounds 12, 14) by a sequence of chemical reactions portrayed in FIG. 2B. Phosphorylation of benzyl 4-bromophenylacetate (compound 6) under nickel chloride catalysis (formation of compound 8 via intermediate compound 7) is of particular importance since it is the crucial step in the reaction scheme not previously known in the art. In all other aspects, the conditions of reactions performed follow protocols generally established in synthetic organic chemistry and any other convenient procedure.

Figure 2A:
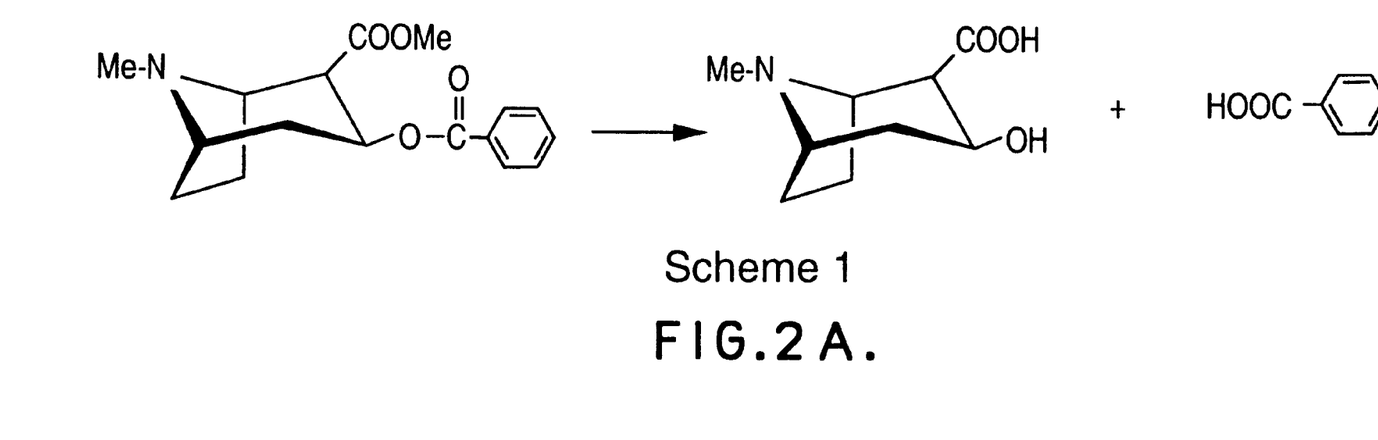
FIG. 2A is a schematic illustration of hydrolysis of cocaine (Scheme 1)

A number of methods known to those skilled in the art may be adapted to follow quantitatively the hydrolysis of cocaine to 2β-methoxycarbonyltropan-3β-ol and benzoic acid by reaction Scheme 1 shown in FIG. 2A. One such method utilizes capillary electrophoresis and detection at $\lambda=200$ nm, as described in detail in Example 9 below and illustrated in FIG. 5. Thus, it is possible to quantitatively measure the hydrolysis of cocaine by either following the loss of cocaine itself, or appearance of the cocaine breakdown products benzoic acid and 2β-methoxycarbonyltropan-3β-ol. The activity of catalytic antibodies and catalytic antisera can be directly related to the activity of naturally occurring esterases, comprising 104-cholinesterase, or control sera.

Protein conjugates 12a,b and 14a,b (see FIG. 2B) of the analogs of transition state for the hydrolysis of the cocaine benzoyl ester are used as immunogens in mice and rabbits. Rabbits provide large volume of antisera and mice provide the potential for generating monoclonal antibodies by conventional hybridoma technology. The esterase activity directed against cocaine benzoyl ester of purified antibodies from either control or immunized rabbits, and from selected hybridomas, was assayed by capillary electrophoresis as described hereinabove. The conjugates 14a,b were endowed with this cocaine esterase activity.

EXAMPLES

The following Examples are used to illustrate the present invention. They should not be construed as limiting it in any way. All parts and percentages are by weight unless otherwise indicated. All abbreviations and acronyms have the standard meanings in the art.

General Chemical Procedures

Melting points were determined on a Reichert-Thermovar melting point apparatus and are not corrected. Optical rotations were measured with a Perkin-Elmer polarimeter (Model 243 B) at 26° C. $^1$H and $^{13}$C NMR spectra were recorded at 300.13 MHz (75.47 MHz, $^{13}$C) or 500.15 MHz (125.04 MHz $^{13}$C) with Bruker spectrometers at the NMR Spectroscopy Laboratory, Carbohydrate Research Centre, University of Toronto. Spectra were obtained at 20° C. either in CDCl$_3$ or CD$_3$OD containing a trace of TMS (0 ppm, $^1$H Examples 1–6

SYNTHESIS OF HAPTENS AND ANTIGENS

Example 1

Figure 2B:
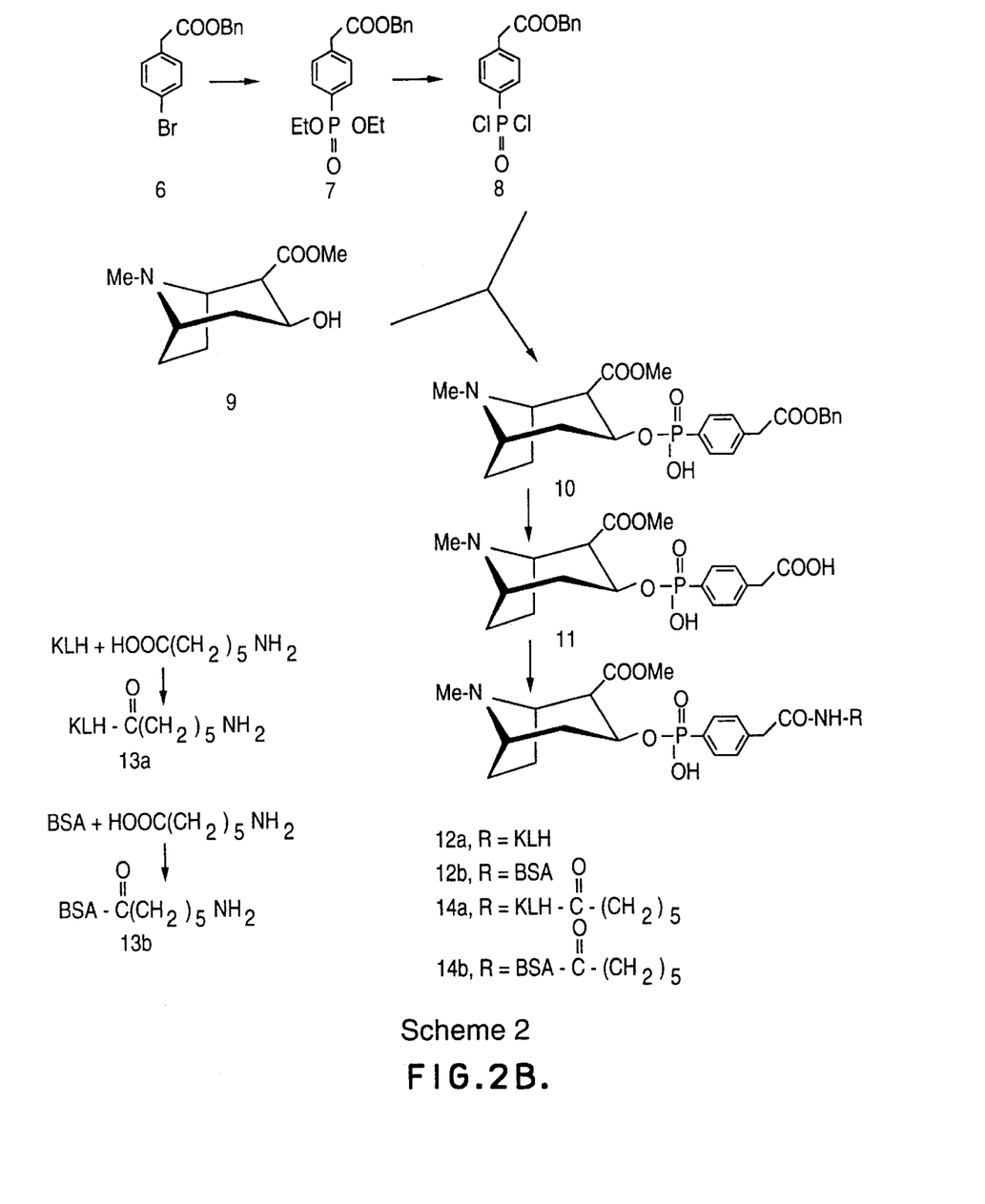
FIG. 2B is a schematic illustration of a synthesis scheme (Scheme 2) for producing cocaine analog conjugate derivatives in accordance with one embodiment of the present invention.

This Example illustrates the preparation of benzyl 4-bromophenylacetate (compound 6, FIG. 2B).

To a suspension of 4-bromophenylacetic acid (2.150 g, 10 mmol) and benzyl alcohol (2.5 mL) in dry dichloromethane (20 mL) was added dicyclohexylcarbodiimide (2.5 g) at 0° C. The mixture was allowed to warm up to room temperature, and stirred overnight. After dilution with dichloromethane (250 mL), the solution was washed with water, dried over sodium sulphate, and dichloromethane was evaporated to give an oily residue. This residue was subsequently subjected to flash chromatography on silica gel using hexane/ethyl acetate (9:1) to give pure compound 6 in 88% yield (3.81 g). $^1$H NMR (CDCl$_3$): 7.47–7.42 (m, 2H), 7.31–7.40 (m, 5H) 7.15–7.17 (m, 2H), 5.16 (s, 2H), 3.61 (s, 2H).

Example 2

This Example illustrates the preparation of benzyl 4-(diethylphosphonyl-)phenylacetate (compound 7, FIG. 2B).

Triethylphosphite (10 mL) was added dropwise to a mixture of compound 6 (7.51 g, 20 mmol) and nickel chloride (0.5 g) heated at 160° C., and the reaction continued to be heated to this temperature for additional 3 hours. Then the mixture, cooled to room temperature, was diluted with dichloromethane (250 mL) and filtered through a celite bed. The filtrate was washed with water, dried over sodium sulphate and evaporated to dryness. The oily residue was purified by flash chromatography on silica gel using ethyl acetate to give pure compound 7 (7.11 g, 81% yield). $^1$H NMR (CDCl$_3$): 7.86–7.77 (m, 2H), 7.45–7.42 (m, 2H), 7.30–7.40 (m, 5H), 5.15 (s, 2H), 4.10–4.20 (m, 6H), 3.70 (s, 2H), 1.38 (t, J=6 Hz 9H). Exact mass measurement (EI): for $C_{18}H_{23}O_5P$ calc. 362.1283, found 362.1267.

Example 3

This Example illustrates the preparation of 2β-(methyloxycarbonyl-)tropan-3β-yl 4-(benzyloxycarbonylmethyl-) phosphonate (compound 10, FIG. 2B).

A mixture of compound 7 (2.80 g, mmol) and trimethylsilyl bromide (TMSBr; 2.01 g) was stirred under argon overnight at room temperature. The excess TMSBr was removed in vacuo, and to the residue was added imidazole (25 mg) and oxalyl chloride (1 mL) and the resulting solution was stirred overnight at room temperature. Then both the solvent and volatiles were evaporated in vacuo and the resulting crude dichloride 8 (FIG. 2B) was diluted with pyridine (10 mL) and added to a solution of triazole (1.0 g) in pyridine (20 mL) and stirred for 30 minutes. Then ecgonine methyl ester (compound 9, FIG. 2B; 1.81 g) was added to this solution and the reaction mixture was stirred for 1 hour at room temperature. The reaction mixture was diluted with 1M TEABC buffer (50 mL) and the resulting solution was extracted with chloroform (7×50 mL). The combined chloroform extracts were evaporated to dryness in vacuo to give compound 10 in 71% yield (2.98). $^1$H NMR (CDCl$_3$): 7.77–7.62 (m, 27.41–7.12 (m, 7H), 5.11 (s, 2H), 4.50 (m, 1H), 3.70 (s, 3H), 3.55 (s, 2H), 2.40 (s, 3H). $^1$H NMR (D$_2$O): 7.80–7.70 (m, 2H), 7.50–7.41 (m, 7H), 5.21 (s, 2H), 4.62–4.59 (m, 1H), 4.02 (d, J=6.7 Hz, 1H), 3.95 (d, J=7 Hz, 1H), 3.88 (s, 3H), 3.72 (s, 2H), 3.10 (dd, J=9 Hz, 2Hz, 1H), 2.80 (s, 3H). Exact mass measurement (FAB): for $C_{25}H_{31}NO_7P$ calc. 468.1838, found 488.1819.

Example 4

This Example illustrates the preparation of 2β-(methyloxycarbonyl-)tropan-3β-yl 4-(methylcarboxyl-) phosphonate (compound 11, FIG. 2B).

To a solution of the compound 10 (750 mg) in glacial acetic acid (15 mL) was added Pd/C (10%; 100 mg) and the mixture was hydrogenated in a Parr instrument overnight. Then the mixture was diluted with dichloromethane (250 mL), the solution was filtered through a celite bed, and the filtrate was evaporated to dryness in vacuo to give compound 11 (700 mg). $^1$H NMR (D$_2$O): 7.73–7.66 (m, 2H), 7.45–7.40 (m, 2H), 4.65–4.58 (m, 1H), 4.10 (d, J=7.20, 1H), 3.95 (d, J=6.80, 1 H), 3.77 (s, 3H), 3.755 (s, 2H), 3.49 (dd J=11, 1.5 Hz, 1H), 2.80 (s, 3H). Exact mass measurement (FAB): for $C_{18}H_{24}NO_7PNa$ calc. 420.1188, found 420.1157.

Example 5

This Example illustrates the preparation of protein conjugates 12a and 12b (FIG. 2B).

Compound 11 (30 mg), KLH (30 mg) and dimethylamino-propyl-3-ethylcarbodiimide hydrochloride (20 mg) was dissolved in water (20 mL) and adjusted to pH=5 by TEABC buffer. After stirring this solution at room temperature for 48 hours, it was filtered through YM-30 (Amicon) membrane filter using 3×10 mL distilled water. The membrane filter was decanted with distilled water 3×10 mL, and the aqueous solution after lyophilization to dryness gave protein conjugate 12a. Using BSA instead of KLH, protein conjugate 12b was obtained.

Example 6

This Example illustrates the preparation of protein conjugates 14a and 14b (FIG. 2B).

A solution of 6-aminocaproic acid (3.0 g), KLH (500 mg) and dimethylamino-propyl-3-ethylcarboiimide hydrochloride (1.0 g) in water (50 mL), adjusted to pH=5 by TEABC buffer, was stirred for 48 hours. Then it was filtered through YM-30 (Amicon) membrane filter using 3×10 mL distilled water. The membrane filter was decanted with distilled water 3×10 mL, and the aqueous solution after lyophilization to dryness gave 6-aminocaproyl KLH (compound 13a, FIG. 2B). Using BSA (0.5 g) instead of KLH, compound 13b, FIG. 2B, was obtained.

A reaction of free carboxyl-containing compound 11 (70 mg) and 6-aminocaproyl KLH (compound 13a) (50 mg) according to the procedure used to synthesize 12a and 12b (as described in Example 5), gave protein conjugate 14a. Under identical conditions, compound 11 reacted with 6-aminocaproyl BSA (compound 13b) to give protein conjugate 14b.

General Immunological Procedures
Antibody purification protocol

Antibodies were purified from rabbit sera using Protein A Sepharose chromatography. Briefly, serum was diluted 1/10 with 50 mM Tris/150 mM NaCl (pH=8.6) and loaded slowly onto a Protein A Sepharose column. After all the material was loaded, the column was washed with 3 column volumes of 50 mM Tris/150 mM NaCl (pH=8.6). Bound antibodies were eluted with 50 mM sodium acetate/150 mM NaCl buffer (pH=3.5) after the column had been washed sequentially with 50 mM sodium phosphate/150 mM NaCl buffer (pH=7.0) and 50 mM sodium citrate/150 mM NaCl buffer (pH=5.5). Eluted antibodies were dialyzed against 5 mM sodium borate buffer (pH=8.3) and quantified using extinction coefficient of 1.43 at 280 nm for a 0.1% solution (1 mg/mL).

Enzyme-Linked ImmunoSorbent Assay (ELISA) Protocol

ELISA assays were used to determine by titration the level of hapten-specific antibody in the sera of immunized animals. Ninety-six well ELISA plates (NUNC-MaxiSorp) were coated with 100 μL of 10 μg/mL hapten-conjugate in 20 mL sodium carbonate buffer (pH=9.6) overnight (16 hours). Excess reactants were washed away with 0.05% Tween 80 in phosphate buffer saline (pH=7.2; PBS/Tween) using a Corning plate washer. Residual protein-binding sites on the ELISA plates were blocked by coating the wells with 1% low-fat milk in PBS (pH=7.2) for 30 minutes, and washing the plates again. Diluted [1/8→1/16,384 with PBS, pH=8.0] sera (50 μL) were added to the wells and incubated at 37° C. for 1 hour. Then wells were washed 3× with PBS/Tween and stained with either goat anti-rabbit or goat anti-mouse IgG (as appropriate) conjugated to alkaline phosphatase (diluted 1/1,000 from commercial stock with 1% low-fat milk in PBS). Plates were incubated at 37° C. for one hour and washed 3× with PBS/Tween and then stained with substrate (p-nitrophenyl phosphate) at 1 mg/mL in 100 mM diethanolamine with 5 mM $MgCl_2$ added. Plates were read at 405 nm using a Titertek Multiskan ELISA plate reader. The animals immunized with protein conjugate 14a (KLH long linker) or with protein conjugate 12a (KLH short linker) were assayed against protein conjugate 14b (BSA short linker); likewise animals immunized with either protein conjugate 14b (BSA long linker) or protein conjugate 12b (BSA short linker) were assayed against 14a protein conjugate (KLH long linker).

Capillary Electrophoresis Protocol

Capillary electrophoresis was used to monitor the breakdown of cocaine by separately monitoring the presence of cocaine and its breakdown products, methyl ecgonine and benzoic acid, in the reaction mixture. Using a Beckman P/ACE System 2100 capillary electrophoresis apparatus and a fused silica column (57 cm long) with an internal diameter of 75 μm, all samples were analyzed in either 5 mM or 100 mM borate buffer (pH=8.3). Specimens of cocaine (0.5 mM) were incubated at room temperature with either horse serum ψ-cholinesterase (25 units; Sigma Chemicals), or purified rabbit antibodies. Material was loaded onto the column using low (0.5 psi) pressure injection (4 seconds long) and separated under influence of 24 kV at 25° C. Peaks were read at 200 nm and analyzed using Beckman System Gold software (version 7.01).

Examples 7–10
PREPARATION OF ANTISERA AND ANTIBODIES

Example 7

This Example shows the effect of immunization of mice with the different hapten carrier conjugates.

Twenty BALB/c mice (female; 4–6 weeks old) were each immunized subcutaneously with 50 μg of hapten-conjugates (cf. Table 1 below) in PBS (pH=7.2; 25 μL) emulsified with an equal volume of Freund's complete adjuvant on day 0. All animals were boosted intraperitoneally with an equivalent amount of the corresponding hapten-conjugate emulsified this time with Freund's incomplete adjuvant on day 28. All animals were bled from the retro-orbital plexus on day 42 (2 weeks after boosting) and sera were tested for hapten-specific antibodies by ELISA. The same four different hapten-conjugates, as were used with the rabbits, were tested in each of four different groups of five animals each as summarized in Table 1 below.

FIG. 3 shows graphically the results of the determination by ELISA titration analysis of the level of anti-cocaine analog activity responses in individual mice, with each mouse being indicted by a separate symbol, to immunization by one of the different hapten-carrier conjugates.

Figure 3A:
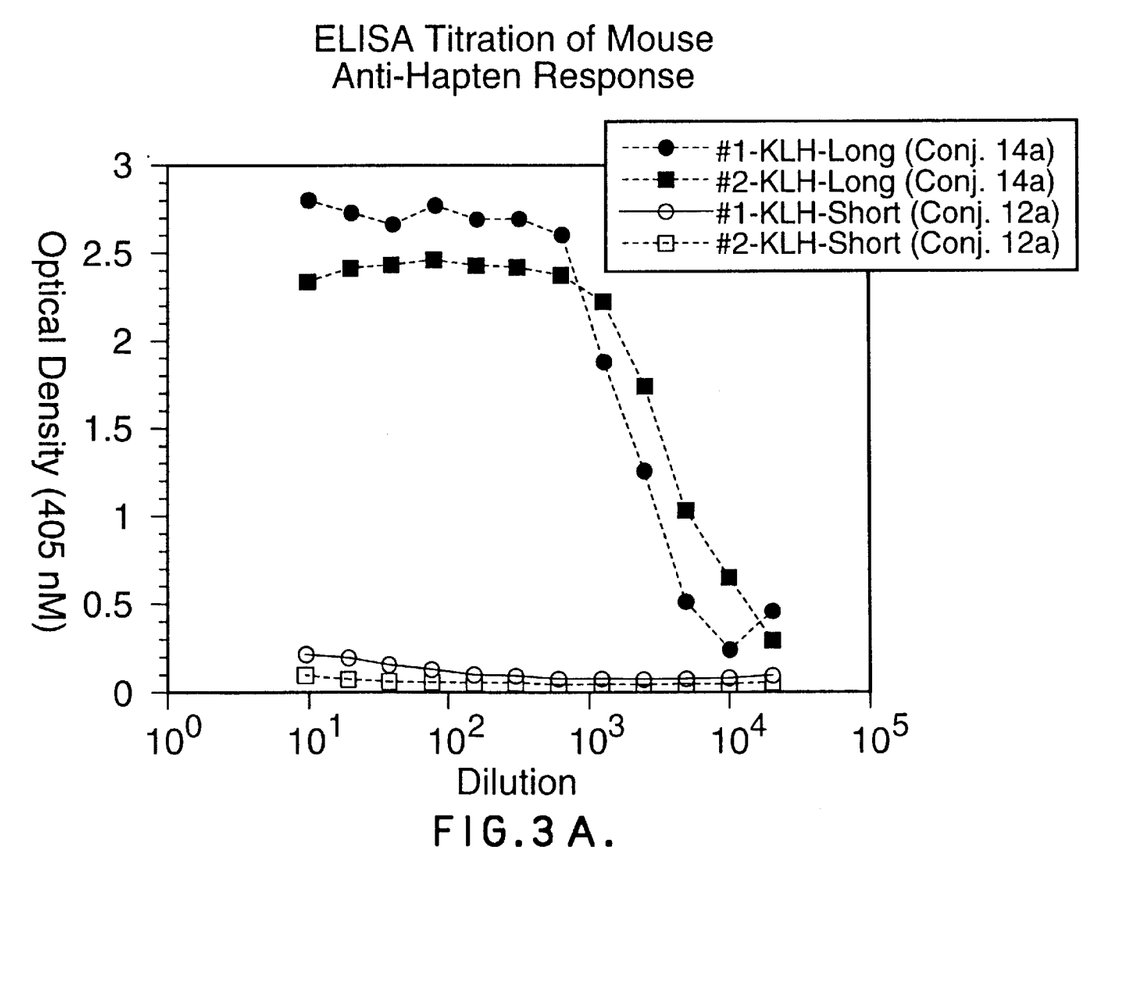
FIGS. 3A and 3B contain graphical representations of an ELISA titration of mouse anti-hapten response to cocaine analog conjugate derivatives provided in accordance with one embodiment of the invention.
Figure 3B:
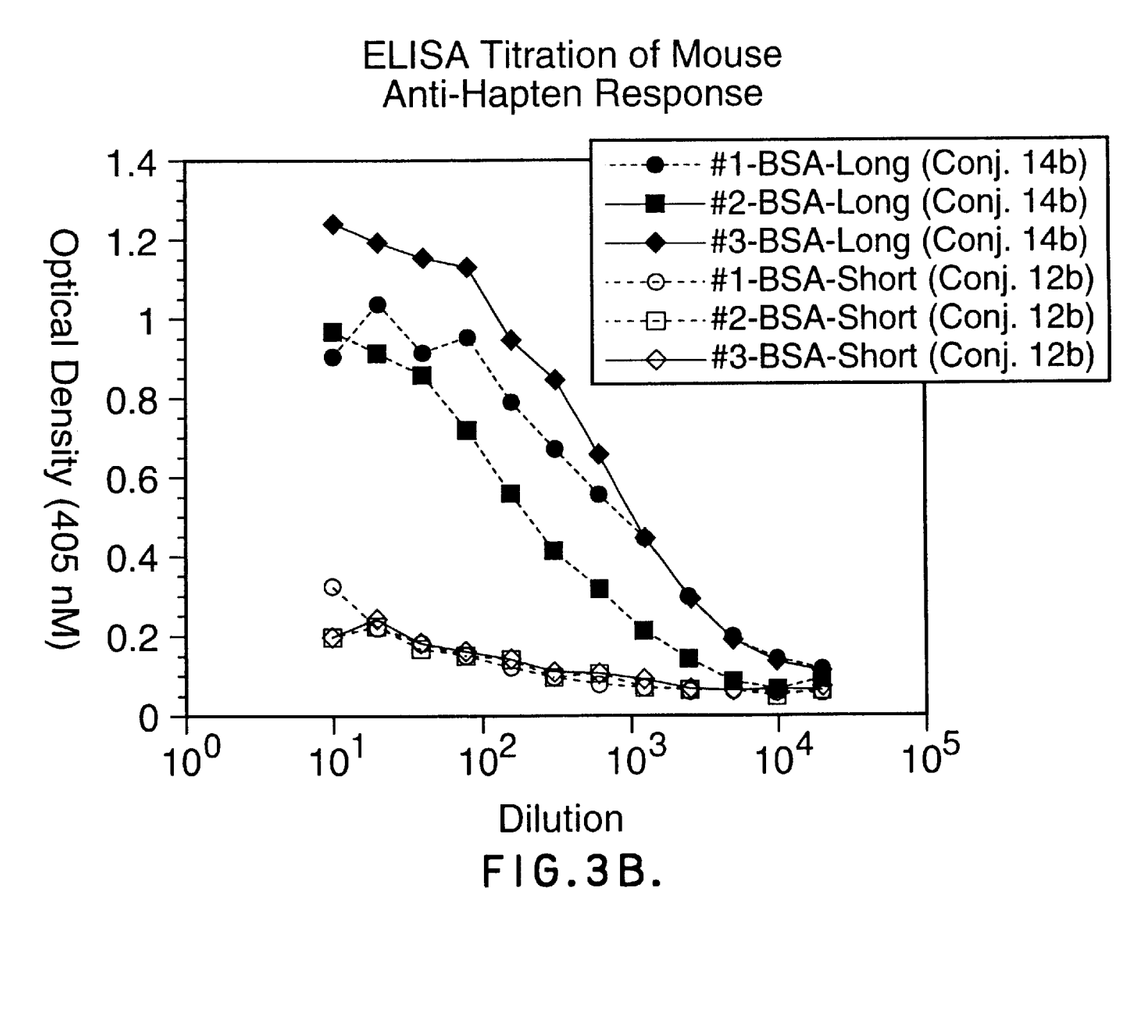

The upper panel A illustrates the anti-hapten response to the KLH-long (conjugate 14a) and KLH-short (conjugate 12a) conjugates assayed on the BSA-long (conjugate 14b) conjugate. The lower panel B illustrates the anti-hapten response to the BSA-long (conjugate 14b) and BSA-short (conjugate 12b) conjugates assayed on the KLH-long (conjugate 14a) conjugate.

Figure 4:
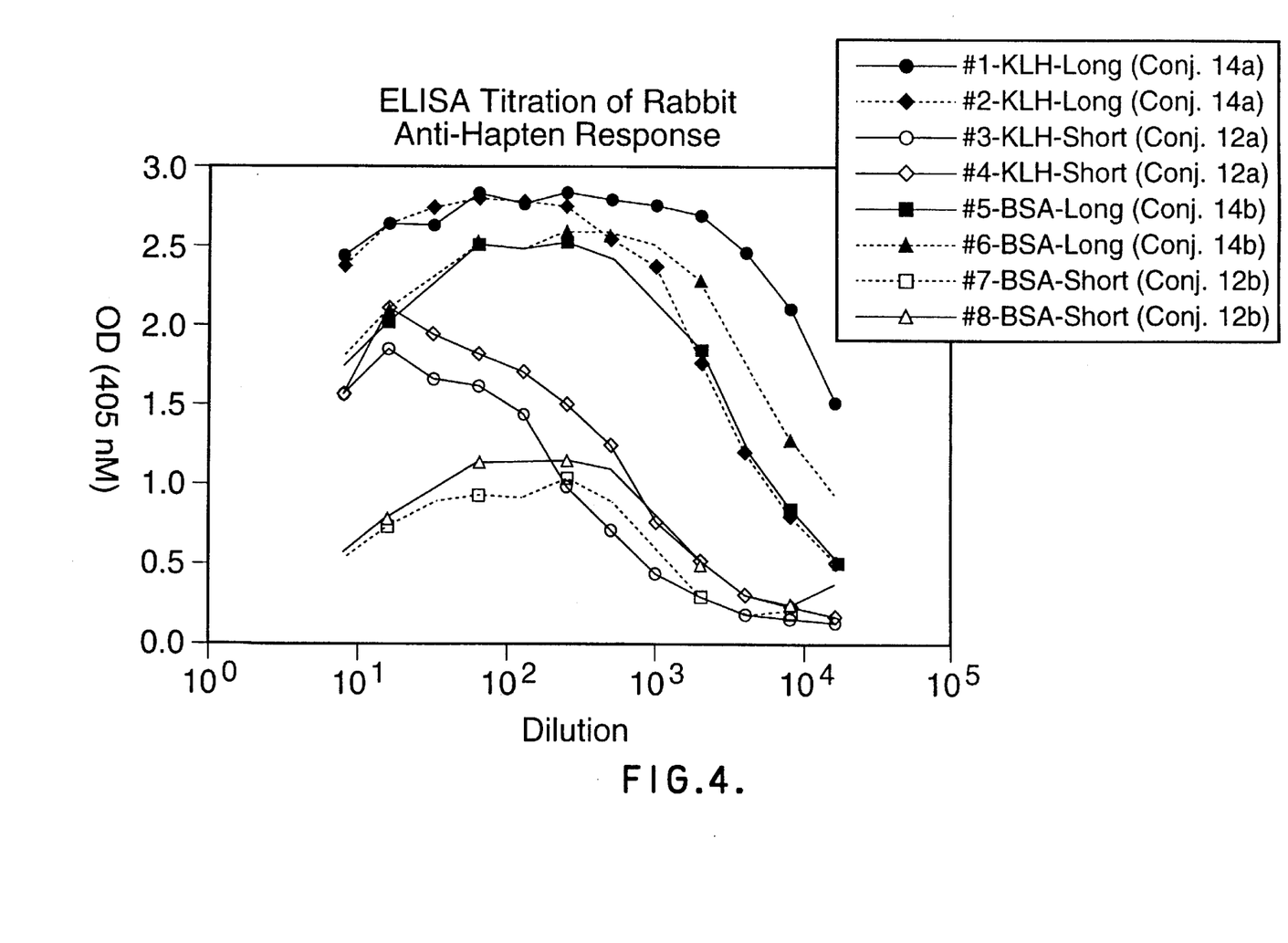
FIG. 4 contains graphical representations of an ELISA titration of rabbit anti-hapten response to cocaine analog conjugate derivatives provided in accordance with one embodiment of the invention.

Collectively, the data presented in FIG. 4 indicate that the cocaine analog hapten-protein carrier conjugates are more effective at inducing anti-hapten responses when the analog is conjugated to the carrier protein by the long linker.

Example 8

This Example shows the effect of immunization of rabbits with the different hapten carrier conjugates.

Eight New Zealand White rabbits (female; 2.5 kg each) were immunized in three sites (one subcutaneous, two intramuscular) with a hapten-conjugate (500 μg) in PBS (pH=7.2; 250 μL), emulsified with an equal volume of Freund's complete adjuvant on day 0. All animals were boosted with an equivalent amount of the corresponding hapten-conjugate emulsified this time with Freund's incomplete adjuvant, again in three different sites (one subcutaneous, two intramuscular) on day 28. All animals were bled from the marginal ear vein on day 42 (two weeks after boosting) and sera were tested for hapten specific antibodies by ELISA. Four different hapten-conjugates were tested, each in two rabbits, as summarized in the following Table 1:

TABLE 1

| Hapten-conjugate | Recipients |
| --- | --- |
| 14a (KLH long linker) | Rabbits #1&2; five mice |
| 12a (KLH short linker) | Rabbits #3&4; five mice |
| 14b (BSA long linker) | Rabbits #5&6; five mice |
| 14b (BSA short linker) | Rabbits #7&8; five mice |
| Unimmunized control | Rabbit #9; five mice |

Example 9

This Example illustrates an assay by capillary electrophoresis of the degradation of cocaine by the enzyme ψ-cholinesterase.

Figure 5A:
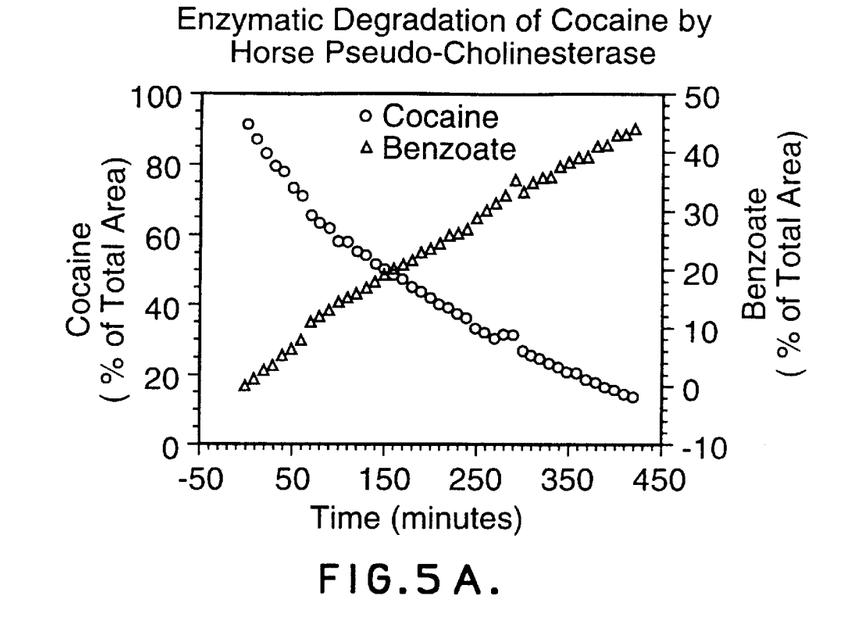
FIGS. 5A and 5B contain graphical representation of capillary electrophoresis monitoring of the rate of enzymatic degradation of cocaine into ester hydrolysis products.

Capillary electrophoresis was used to monitor the rate of enzymic degradation by 25 units of horse ψ-cholinesterase (Sigma) of 0.5 mM cocaine at 25° C. in borate buffer pH 8.3 into products of the ester hydrolysis, namely methyl ecgonine and benzoate (Scheme 1, FIG. 2A), by measuring the diminishing area under the cocaine peak and the growing area under benzoate peak. The results obtained are shown in the upper panel A of FIG. 5.

Figure 5B:
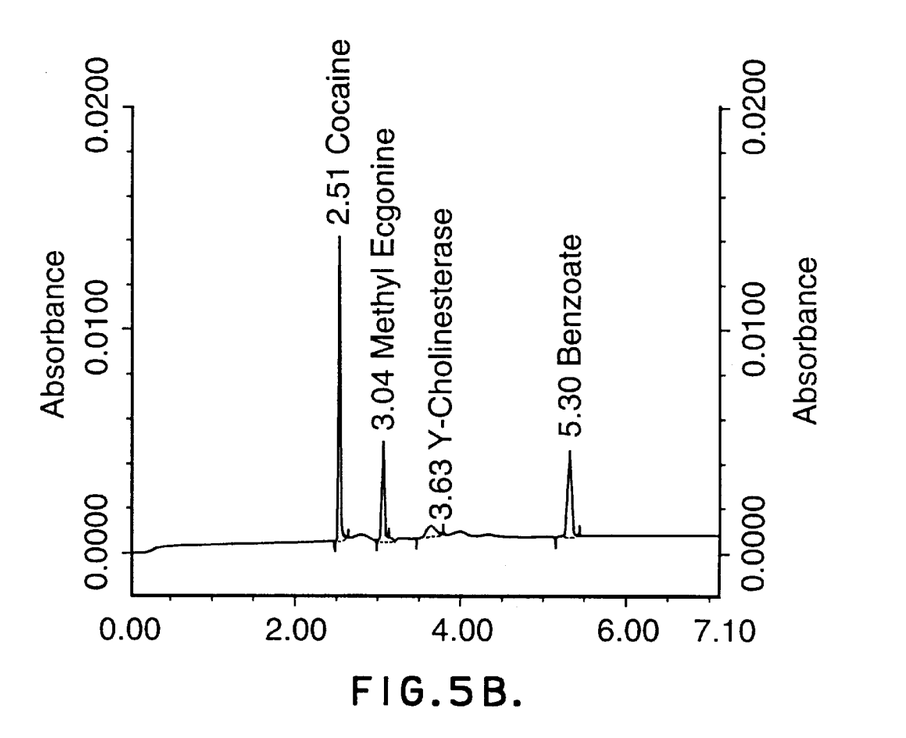

A representative tracing of the capillary electrophoresis pattern for one of these time points illustrated in the lower panel B of FIG. 5.

Example 10

This Example illustrates an assay by capillary electrophoresis of the degradation of cocaine by antibodies from the hapten-conjugate-immunized rabbits.

Figure 6A:
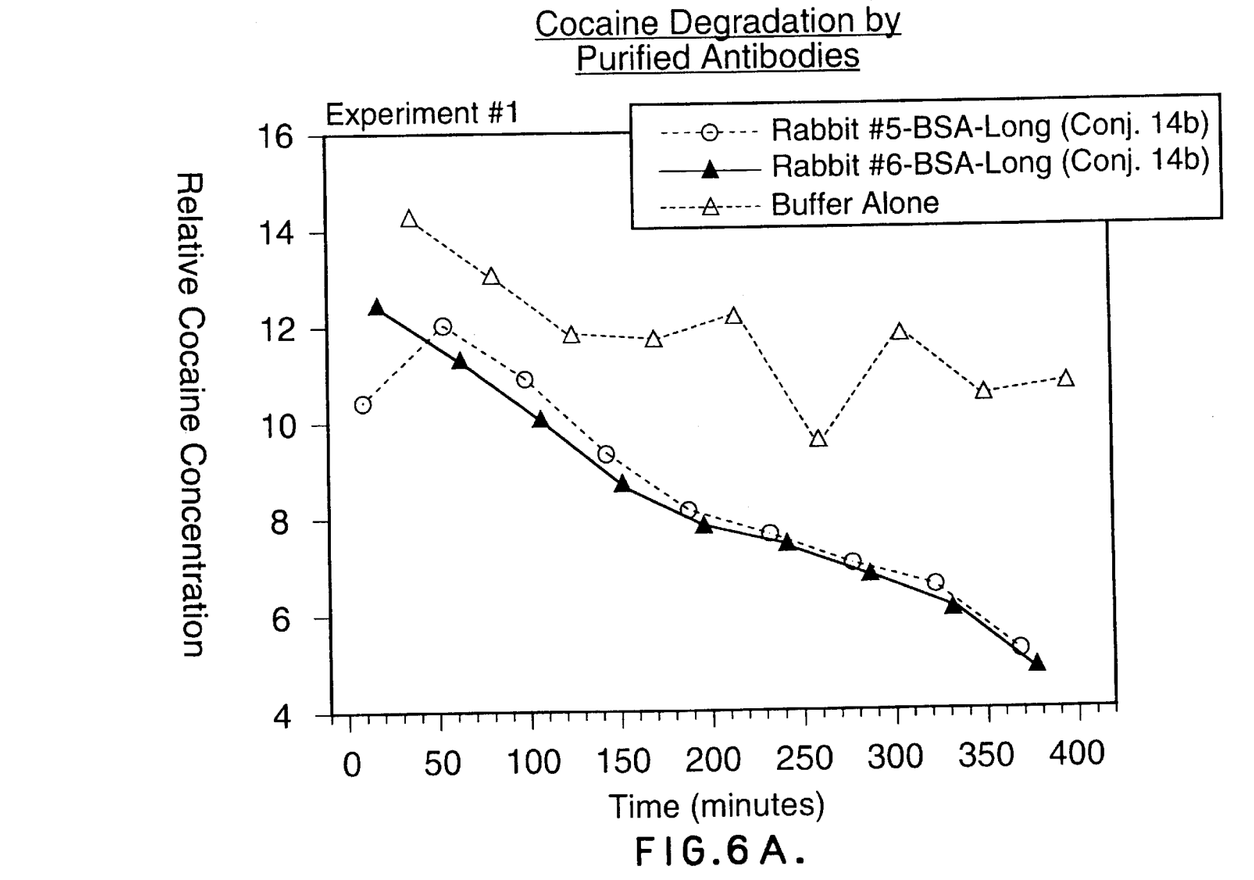
FIGS. 6A and 6B contain graphical representation of capillary electrophoresis monitoring of the rate of degradation of cocaine by antibodies raised against cocaine analog conjugate derivatives.

A capillary electrophoresis analysis of the degradation of cocaine by purified rabbit antibodies isolated from a control unimmunized rabbit and rabbits immunized by the BSA-long conjugate (conjugate 14b), as in Example 8 above. The results obtained are shown in FIG. 6. The upper panel A shows the rate of degradation of 0.5 mM cocaine at 24° C. in borate buffer pH 8.3 for two immunized rabbits and that the breakdown was significantly greater for such rabbits than for the breakdown of cocaine alone in buffer.

Figure 6B:
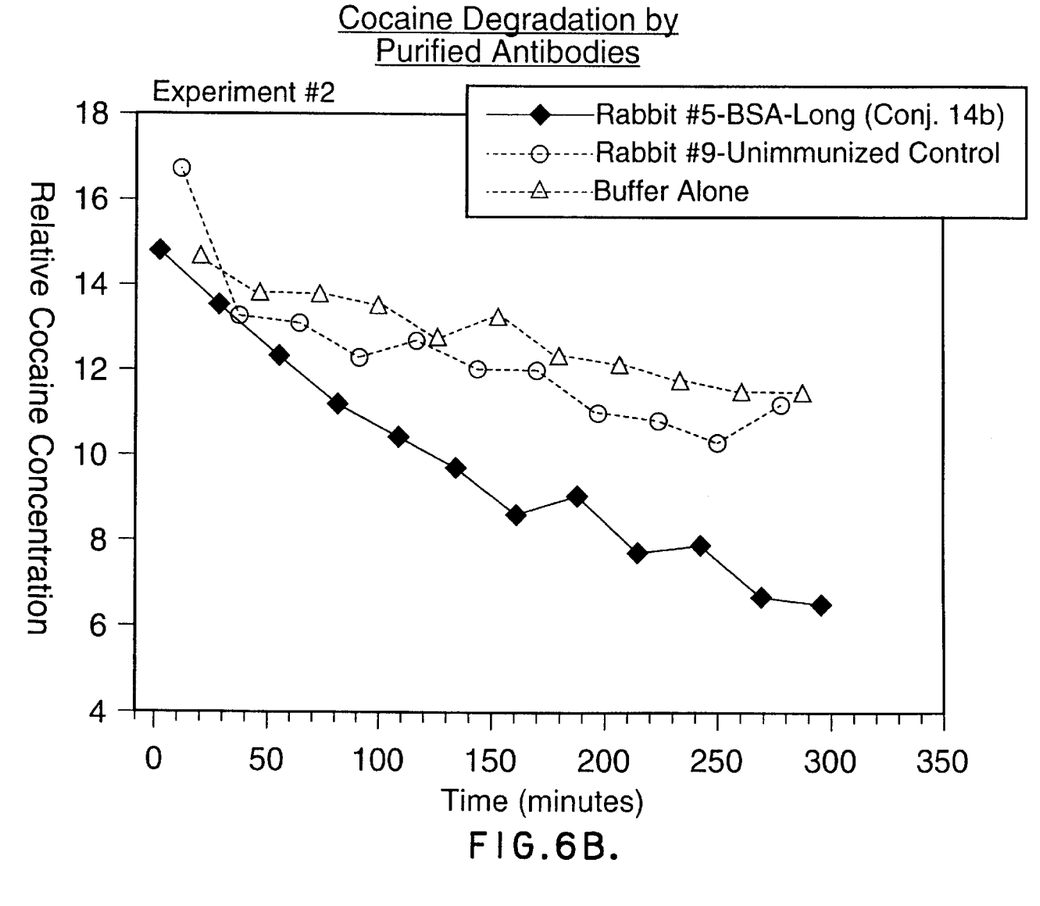

In the lower panel B, the immunized rabbit antibodies were also more effective than antibodies from an unimmunized animal, which was not significantly different from buffer alone. These data show that the animals immunized with the BSA-long conjugates of the cocaine analog possessed antibodies which were able to catalyze the breakdown of cocaine.

SUMMARY OF DISCLOSURE

While the present invention has been described with reference to specific embodiments thereof, it should be understood by those skilled in the art that various changes may be made and equivalents may be substituted without departing from the true spirit and scope of the invention. In addition, many modifications may be made to adapt a particular situation, material or composition of matter, process, process step or steps, or then present objective to the spirit of this invention without departing from its essential teachings.

REFERENCES

1. F. I. Carroll and A. H. Lewin, in Emerging Technologies and New Directions in Drug Abuse Research (R. S. Rapaka, A. Makriyannis, and M. J. Kuhar, Eds.), NIDA Research Monograph #112, Superintendent of Documents, U.S. Government Printing Office, Washington D.C. 1991, 284–299.
2. K. D. Janda, S. J. Benkovic, and R. A. Lerner, Science 244, 437–440 (1989).
3. S. J. Pollack, P. Hsiun, and P. G. Schultz, J. Am. Chem. Soc. 111, 5961–5962 (1989).
4. N. S. Chandrakumar, C. C. Carron, D. B. Meyer, P. M. Beardsley, S. A. Nash, L. L. Tam, and M. Rafferty, Bioorg. Med. Chem. Lett. 3, 309–312 (1993).
5. D. W. Landry, K. Zhao, G. X.-Q. Yang, M. Glickman, T. M. Georgiadis, Science 259, 1899–1901 (1993).
6. M. Y. Meah, D. L. Skea, W. A. Corrigall, B. H. Barber, and J. J. Krepinsky, unpublished observations.

What we claim is:

1. An ecgonine phosphonate ester of the formula:

wherein said carrier molecule is a peptide, polypeptide or protein and n is a value so as to provide a linker group having a total of 5 to 15 linear atoms between said carrier molecule and the benzene ring.

2. The compound of claim 1 wherein the total number of linear atoms in said linker group is from about 8 to about 10 atoms.

3. An immunogenic composition useful in the treatment of an animal, which comprises an effective amount of a compound according to claim 1 or an antibody raised thereto, and a pharmaceutically-acceptable carrier.

4. An ecgonine phosphonate ester of the formula:

5. The ecgonine phosphonate ester of claim 4 wherein the free carboxyl group is protected.

* * * * *